US008897849B2

(12) United States Patent
Shirasaki et al.

(10) Patent No.: US 8,897,849 B2
(45) Date of Patent: Nov. 25, 2014

(54) CARDIOVASCULAR RISK EVALUATION APPARATUS

(75) Inventors: Osamu Shirasaki, Tokyo (JP); Mitsuo Kuwabara, Osaka (JP); Kazuomi Kario, Tochigi (JP)

(73) Assignees: Omron Healthcare Co., Ltd., Kyoto (JP); Jichi Medical University, Tochigi (JP)

( * ) Notice: Subject to any disclaimer, the term of this patent is extended or adjusted under 35 U.S.C. 154(b) by 0 days.

(21) Appl. No.: 14/116,928

(22) PCT Filed: May 16, 2012

(86) PCT No.: PCT/JP2012/062504
§ 371 (c)(1),
(2), (4) Date: Nov. 11, 2013

(87) PCT Pub. No.: WO2012/161047
PCT Pub. Date: Nov. 29, 2012

(65) Prior Publication Data
US 2014/0088386 A1 Mar. 27, 2014

(30) Foreign Application Priority Data

May 24, 2011 (JP) ................................. 2011-115845

(51) Int. Cl.
*A61B 5/1455* (2006.01)
*A61B 5/0205* (2006.01)
*A61B 5/00* (2006.01)
*A61B 5/022* (2006.01)

(52) U.S. Cl.
CPC .............. *A61B 5/7275* (2013.01); *A61B 5/0205* (2013.01); *A61B 5/022* (2013.01); *A61B 5/1455* (2013.01); *A61B 5/14552* (2013.01); *A61B 5/4809* (2013.01); *A61B 5/4818* (2013.01); *A61B 5/742* (2013.01)
USPC .......................................... 600/324; 600/483

(58) Field of Classification Search
CPC .... A61B 5/0205; A61B 5/022; A61B 5/1455; A61B 5/14551; A61B 5/14552; A61B 5/7271; A61B 55/7275

USPC ......... 600/300, 310, 322, 323, 324, 481, 483, 600/485
See application file for complete search history.

(56) References Cited

U.S. PATENT DOCUMENTS

2012/0065514 A1* 3/2012 Naghavi et al. ............... 600/481
2012/0209082 A1* 8/2012 Al-Ali ............................ 600/300
2014/0073888 A1* 3/2014 Sethi et al. ..................... 600/324

FOREIGN PATENT DOCUMENTS

JP 62-155829 A 7/1987
JP 2009-039352 A 2/2009
JP 2009-066269 A 4/2009

OTHER PUBLICATIONS

International Search Report issued in PCT/JP2012/062504 mailed on Jul. 24, 2012 (3 pages).
Written Opinion of the International Searching Authority issued in PCT/JP2012/062504 mailed on Jul. 24, 2012 (6 pages).

(Continued)

Primary Examiner — Eric Winakur
(74) Attorney, Agent, or Firm — Osha Liang LLP

(57) ABSTRACT

A cardiovascular risk evaluation apparatus includes a hypoxic acquisition unit for acquiring a measurement result that includes a blood oxygen saturation level measured in a hypoxic period in which the blood oxygen saturation level of a subject is lower than a threshold value, and a blood pressure measured when the blood oxygen saturation level was measured; a non-hypoxic acquisition unit for acquiring a measurement result that includes a blood oxygen saturation level measured in a non-hypoxic period of the blood oxygen saturation level of the subject, and a blood pressure measured when the blood oxygen saturation level was measured; and an indicator acquisition unit for acquiring a cardiovascular risk evaluation indicator for the subject based on the relationship between blood oxygen saturation level and blood pressure, which is based on the measurement results acquired by the hypoxic acquisition unit and the non-hypoxic acquisition unit.

8 Claims, 11 Drawing Sheets

(56) References Cited

OTHER PUBLICATIONS

Kario, K..; "Hypertension associated with obstructive sleep apnea syndrome"; Journal of Blood Pressure, vol. 16, No. 3, 2009, pp. 239-243 (5 pages).

Penzel, T. et al.; "Ambulatory Recording of Sleep Apnea Using Peripheral Arterial Tonometry"; 2004 IEEE Engineering in Medicine and Biology 26th Annual Conference vol. V, Sep. 1-5, 2004, pp. 3856-3859 (5 pages).

\* cited by examiner

| No. | Time | F | Sp(i)/MSp(i) | SBP | DBP | PL |
|---|---|---|---|---|---|---|
| 1 | T(1) | 0 | SP(1) | SBP(1) | DBP(1) | PL(1) |
| 2 | T(2) | 1 | MSP(2) | SBP(2) | DBP(2) | PL(2) |
| ⋮ | ⋮ | ⋮ | ⋮ | ⋮ | ⋮ | ⋮ |

|  |  |  |  | ID |
|---|---|---|---|---|
| No. | Time | DF | OS | NH |
| 1 | T(1) | DF(1) | OS(1) | 1 |
| 2 | T(2) | DF(2) | OS(2) | 0 |
| ⋮ | ⋮ | ⋮ | ⋮ | ⋮ |

*FIG. 7*

CARDIOVASCULAR RISK EVALUATION APPARATUS

TECHNICAL FIELD

The present invention relates to a cardiovascular risk evaluation apparatus that evaluates the cardiovascular risk of a subject, and in particular relates to a cardiovascular risk evaluation apparatus that evaluates cardiovascular risk based on the relationship between the subject's blood oxygen saturation level and blood pressure.

BACKGROUND ART

When obstructive sleep apnea (OSA) occurs, the reduction in blood oxygen saturation level during the apnea attack is accompanied by a rapid rise in blood pressure, and this subjects the cardiovascular system to an immense pressure load. This pressure load is a strong candidate as a mechanism responsible for cerebrovascular disease and cardiovascular events such as myocardial infarction, and the evaluation of the cardiovascular risk of a patient based on information regarding this rise in blood pressure is very important in the management of various types of disorders.

As a conventional method for estimating the cardiovascular risk of an OSA patient, Patent Literature 1 (JP 2009-66269A) proposes a method of continuously measuring the blood oxygen saturation level and finding the time integral of values below a predetermined threshold value. Also, Patent Literature 2 (JP S62-155829A) proposes a method of automatically measuring blood pressure when the blood oxygen saturation level decreases.

CITATION LIST

Patent Literature

Patent Literature 1: JP 2009-66269A
Patent Literature 2: JP S62-155829A

SUMMARY OF INVENTION

Technical Problem

In Patent Literature 1, it is determined that the risk of occurrence of a cardiovascular event is higher the higher the time integral value (IAD) of the blood oxygen saturation levels below the threshold value is. However, since the amount of rise in blood pressure differs from individual to individual even at the same level of decrease in blood oxygen saturation level, the pressure load on the cardiovascular system cannot be accurately evaluated using the IAD, and it is not possible to acquire a cardiovascular risk evaluation indicator that takes pressure load into account.

In Patent Literature 2 (JP S62-155829A), the blood pressure during apnea is simply measured, and therefore it is not possible to assess the responsiveness of the rise in blood pressure in response to the decrease in oxygen saturation level, and it is not possible to acquire a cardiovascular risk evaluation indicator that takes pressure load into account.

In view of this, an object of the present invention is to provide a cardiovascular risk evaluation apparatus that can acquire a cardiovascular risk evaluation indicator that takes into account pressure load in response to a decrease in blood oxygen saturation level.

Solution to Problem

According to one aspect of the present invention, a cardiovascular risk evaluation apparatus includes: a hypoxic acquisition means for acquiring a measurement result that includes a blood oxygen saturation level that is measured in a hypoxic period in which the blood oxygen saturation level of a subject is lower than a threshold value, and a blood pressure that was measured when the blood oxygen saturation level was measured; a non-hypoxic acquisition means for acquiring a measurement result that includes a blood oxygen saturation level that is measured in a non-hypoxic period of the blood oxygen saturation level of the subject, and a blood pressure that was measured when the blood oxygen saturation level was measured; an indicator acquisition means for acquiring a cardiovascular risk evaluation indicator for the subject based on a relationship between blood oxygen saturation level and blood pressure that is based on the measurement result acquired by the hypoxic acquisition means and the measurement result acquired by the non-hypoxic acquisition means; and a means for outputting the acquired indicator to an output unit.

Advantageous Effects of Invention

According to the present invention, it is possible to acquire a cardiovascular risk evaluation indicator that takes pressure load into account based on the relationship between blood oxygen saturation level and blood pressure, which is based on a measurement result that includes a blood oxygen saturation level that is measured in a hypoxic period of a subject and a blood pressure that is measured when that blood oxygen saturation level was measured, and on a measurement result that includes a blood oxygen saturation level that is measured in a non-hypoxic period and a blood pressure that is measured when that blood oxygen saturation level was measured.

BRIEF DESCRIPTION OF DRAWINGS

FIG. 7 is a diagram showing an example of content in an indicator storage portion according to the embodiment.

DESCRIPTION OF EMBODIMENTS

An embodiment of the present invention will be described in detail below with reference to the drawings. Note that like reference signs in the figures denote the same or corresponding portions, and redundant descriptions will not be given for them.

Cardiovascular Risk Evaluation Apparatus

Figure 1:
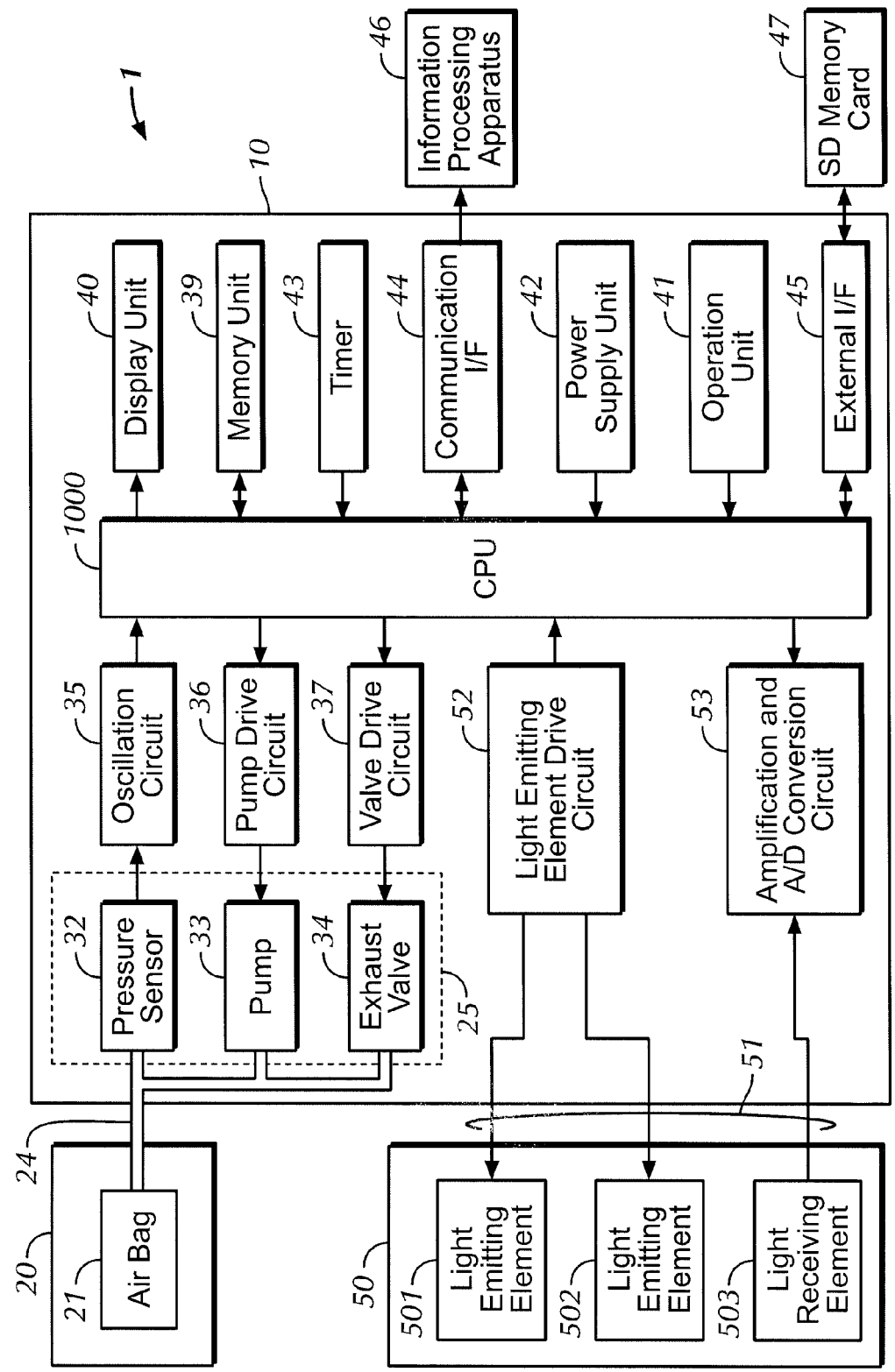
FIG. 1 shows a hardware configuration of a cardiovascular risk evaluation apparatus according to an embodiment.
Figure 2:
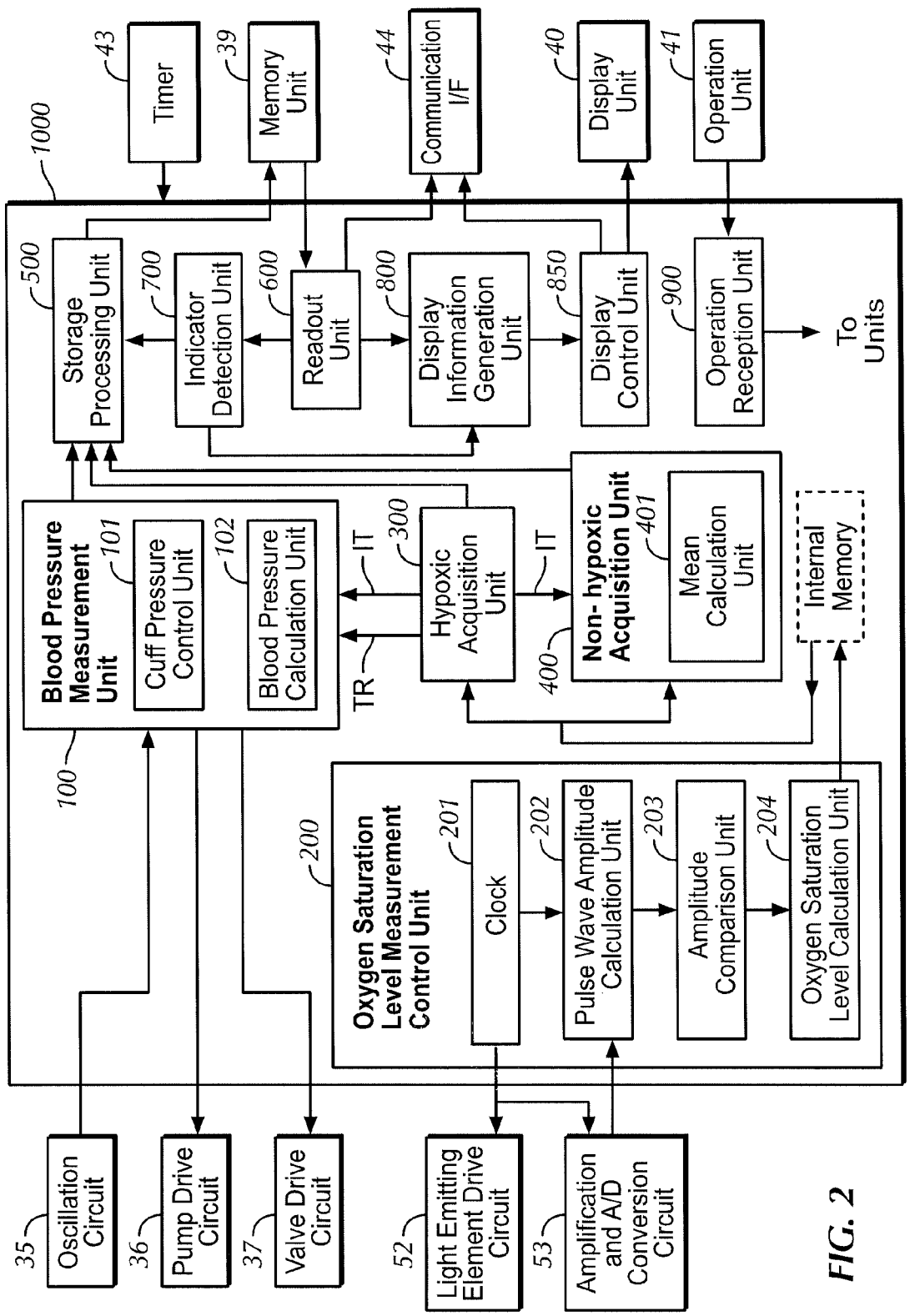
FIG. 2 shows a functional configuration of the cardiovascular risk evaluation apparatus according to the embodiment.
Figure 3:
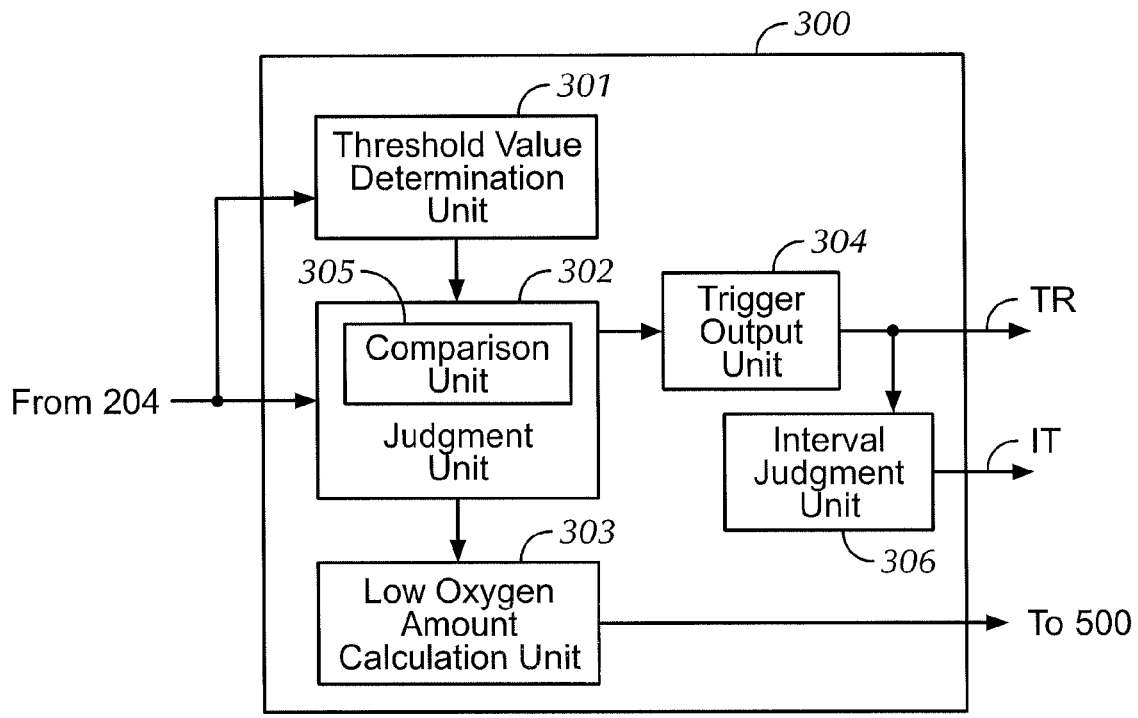
FIG. 3 shows a functional configuration of a hypoxic acquisition unit according to the embodiment.
Figure 4:
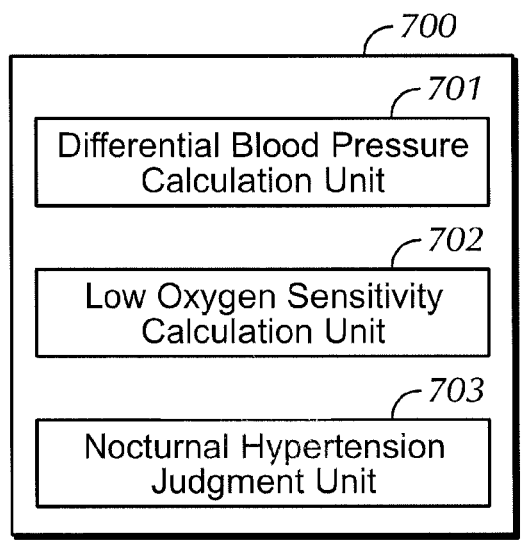
FIG. 4 shows a functional configuration of an indicator detection unit according to the embodiment.
Figures 5, 6:
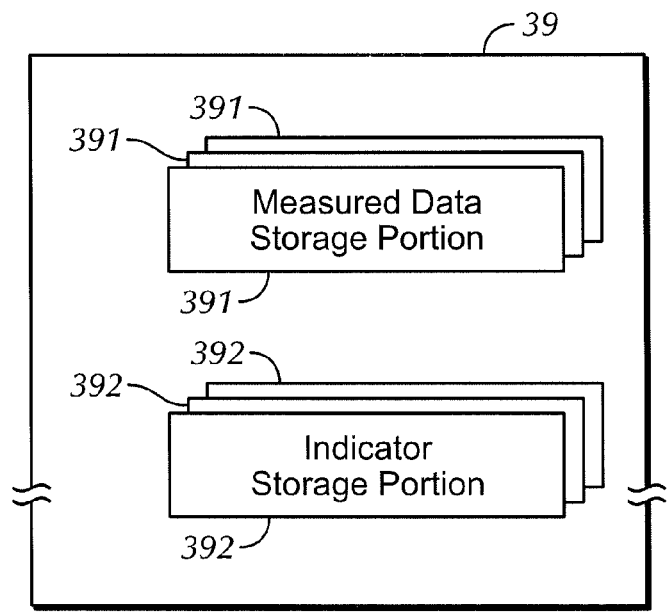
FIG. 5 is a diagram showing an example of content in a memory unit according to the embodiment.
FIG. 6 is a diagram showing an example of content in a measured data storage portion according to the embodiment.
Figure 7:
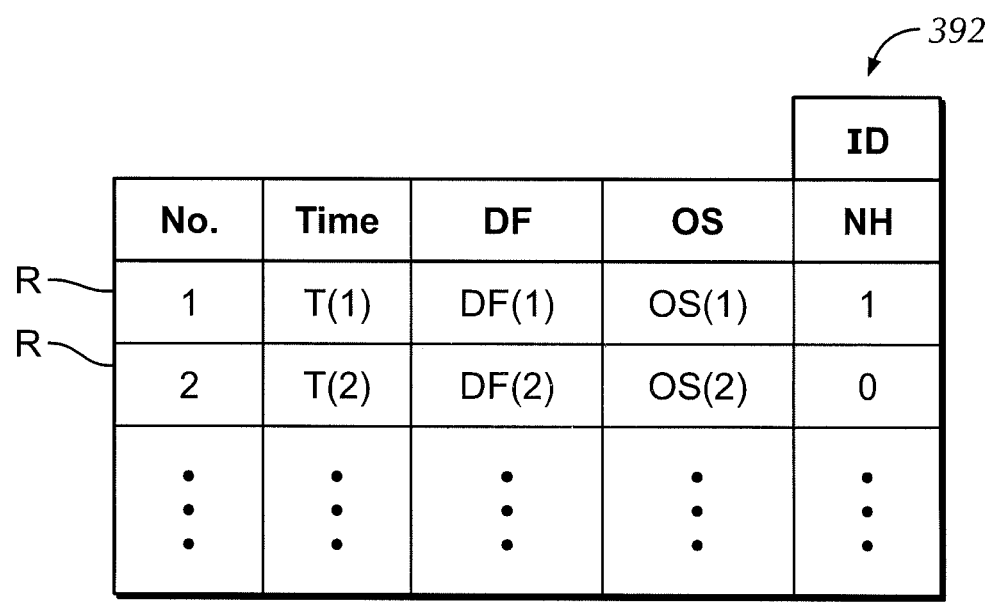
Figure 8A:
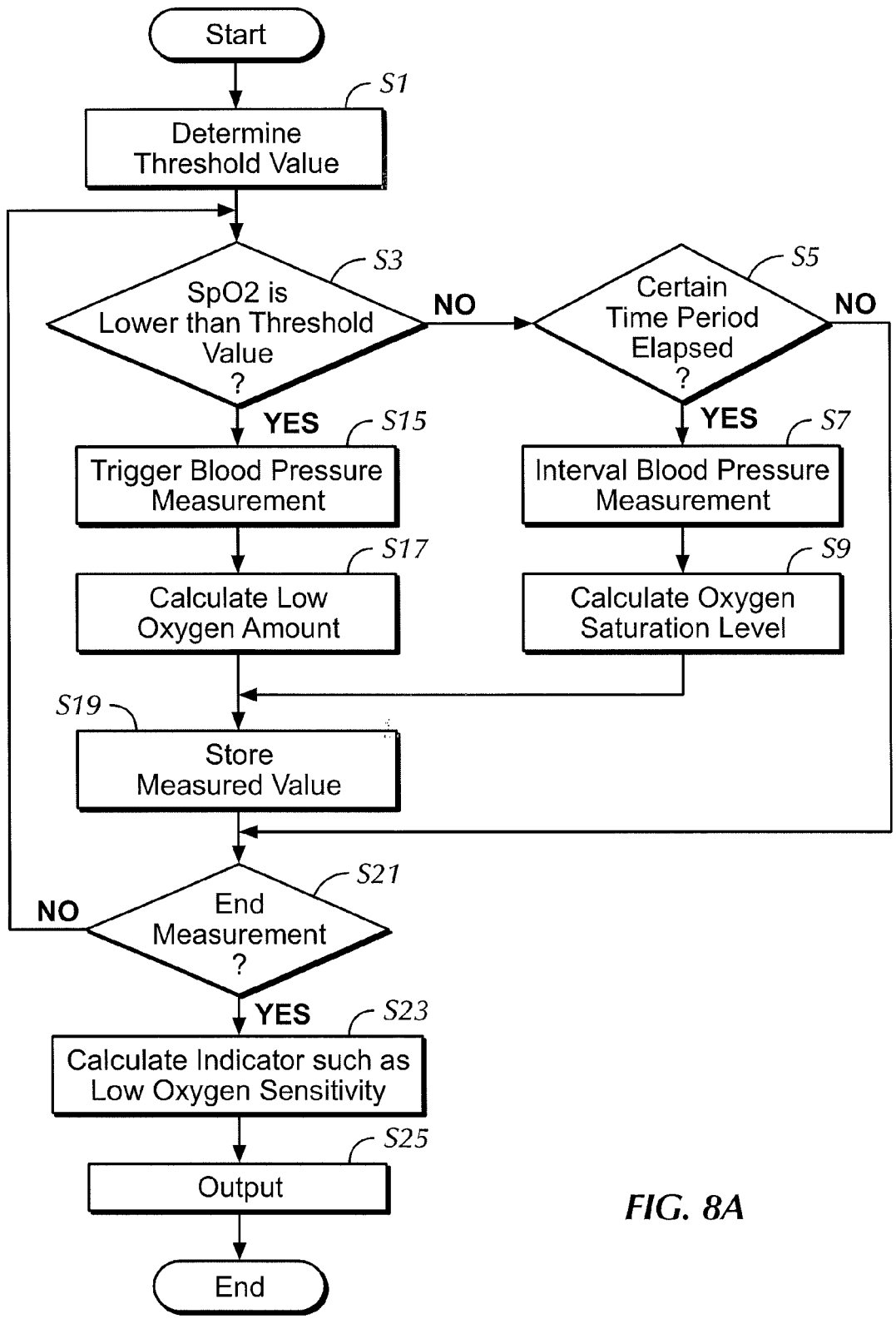
FIGS. 8A and 8B are respectively a flowchart and a related graph according to the embodiment.
Figure 8B:
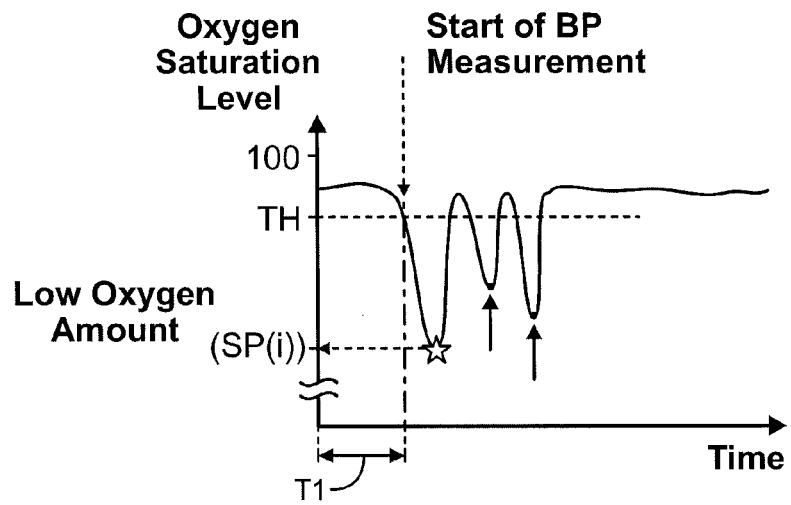
Figure 9:
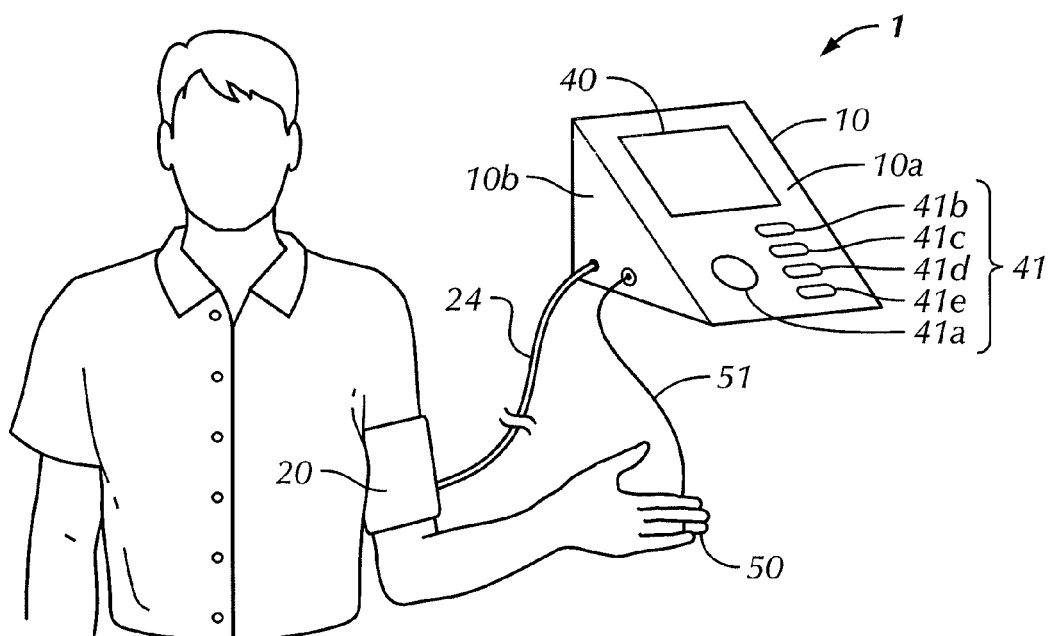
FIG. 9 is an external view of the cardiovascular risk evaluation apparatus according to the embodiment.

FIG. 1 shows the hardware configuration of a cardiovascular risk evaluation apparatus 1 according to the present embodiment, FIGS. 2 to 4 show the overall functions of the cardiovascular risk evaluation apparatus 1 and the configurations of the functions, FIGS. 5 to 7 show examples of content in a memory unit 39 shown in FIG. 1, FIG. 8 shows a processing flowchart, and FIG. 9 schematically shows an external view of the cardiovascular risk evaluation apparatus 1 and how it is used during measurement.

External Appearance

As shown in FIGS. 1 and 9, the cardiovascular risk evaluation apparatus 1 includes a body unit 10, a cuff 20 that is wound around a blood pressure measurement site (e.g., upper arm) on the subject, an air tube 24 for connecting the body unit 10 and the cuff 20, and a sensor unit 50 for fitting on a measurement site for measuring the blood oxygen saturation level (e.g., fingertip). The body unit 10 and the sensor unit 50 are electrically connected via wiring 51.

A surface 10A of the body unit 10 is provided with a display unit 40 for displaying measurement results and the like, and an operation unit 41 for receiving the input of instructions from a user (typically, the subject). The operation unit 41 includes, for example, a switch 41A operated to switch the power on/off, a switch 41B operated to identify the subject, switches 41C and 41D operated to input instructions to start and stop measurement, and a switch 41E operated to input an instruction to readout and display information regarding past measured data. The display unit 40 is configured by a liquid crystal display or the like. The aforementioned air tube 24 and wiring 51 are connected to a left side face 10B of the body unit 10.

Hardware Configuration

As shown in FIG. 1, the cuff 20 of the cardiovascular risk evaluation apparatus 1 includes an air bag 21 that is filled with air. The air bag 21 is connected to an air system 25 built into the body unit 10 via the air tube 24.

The air system 25 includes a capacitance type pressure sensor 32 for detecting the pressure inside the air bag 21 (referred to hereinafter as the "cuff pressure"), a pump 33 for supplying air to the air bag 21, and an exhaust valve 34 that is opened and closed to allow air to flow into or out of the air bag 21.

The sensor unit 50, which corresponds to a so-called pulse oximeter, includes at least two light emitting elements 501 and 502 that emit infrared light having different center wavelengths, and a light receiving element 503 that detects the amount of infrared light that was emitted from the light emitting elements 501 and 502 and passed through the measurement site.

The body unit 10 includes a light emitting element drive circuit 52 that controls the light emitting operation of the light emitting elements 501 and 502, and an amplification and A/D (Analog/Digital) conversion circuit 53 that amplifies the output of the light receiving element 503 separately according to wavelength and subjects it to A/D conversion.

The body unit 10 further includes a CPU (Central Processing Unit) 1000 for performing various types of arithmetic processing, a power supply unit 42, a memory unit 39 that includes a ROM (Read Only Memory), a RAM (Random Access Memory), a non-volatile memory, or the like for storing various types of data and programs, a timer 43, a communication I/F (interface) 44 that controls communication with an information processing apparatus 46 and the CPU 1000, and an external I/F 45 to and from which various types of recording media such as a SD memory card (Secure Digital memory card) can be mounted and removed, and that accesses the mounted recording medium under control of the CPU 1000. Here, there are no limitations on the information processing apparatus 46 as long as it is an apparatus that includes a communication function, a data processing function, and a function for outputting data with a display or the like.

With regard to the air system 25, the body unit 10 includes an oscillation circuit 35, a pump drive circuit 36 for driving the pump 33, and a valve drive circuit 37 for driving the exhaust valve 34.

The pump drive circuit 36 controls the driving of the pump 33 based on a control signal from the CPU 1000. The valve drive circuit 37 controls the opening/closing of the exhaust valve 34 based on a control signal from the CPU 1000.

The capacitance value of the pressure sensor 32 changes according to the cuff pressure, and a signal indicating the capacitance value is output after being amplified by an amplifier (amplification circuit) built into the pressure sensor 32. Based on the output signal from the pressure sensor 32, the oscillation circuit 35 outputs a signal whose oscillation frequency corresponds to the capacitance value of the pressure sensor 32 to the CPU 1000. The CPU 1000 detects the cuff pressure by converting the signal obtained from the oscillation circuit 35 into a pressure.

The power supply unit 42 supplies power to the CPU 1000 in accordance with a power on instruction from the operation unit 41. The CPU 1000 outputs the supplied power to various units.

Functional Configuration

FIG. 2 shows the functional configuration of the CPU 1000 of the cardiovascular risk evaluation apparatus 1 along with circuits in the periphery thereof. As shown in FIG. 2, the CPU 1000 includes the following: a blood pressure measurement unit 100; an oxygen saturation level measurement control unit 200; a hypoxic acquisition unit 300; a non-hypoxic acquisition unit 400 that includes a mean calculation unit 401 for calculating the mean blood oxygen saturation level; a storage processing unit 500 for storing data in the memory unit 39; a readout unit 600 for reading out data from the memory unit 39; an indicator detection unit 700 for detecting an indicator for cardiovascular risk evaluation; a display information generation unit 800 that has a VRAM (Video Random Access Memory) or the like for generating display information to be displayed on the display unit 40; a display control unit 850 that has a digital signal processing circuit or the like for controlling the display on the display unit 40; and an operation reception unit 900 that receives user operations performed using the operation unit 41 and outputs instructions (commands) corresponding to the operations to various units. These units are configured using programs and data stored in the memory unit 39 and/or circuit modules.

The blood pressure measurement unit 100 includes a cuff pressure control unit 101 and a blood pressure calculation unit 102. The cuff pressure control unit 101 adjusts the cuff pressure in the cuff 20 by controlling the operations of the pump drive circuit 36 and the valve drive circuit 37. The blood pressure measurement unit 100 receives an output signal from the oscillation circuit 35, detects the oscillation frequency of the received signal, and converts the detected oscillation frequency into a pressure value signal. The blood pressure measurement unit 100 includes an HPF (High Pass Filter) unit that extracts and outputs a volume pulse wave signal by performing HPF processing on the pressure value signal, and an LPF (Low Pass Filter) unit that extracts and outputs a pressure absolute value signal (referred to hereinafter as the "cuff pressure signal") by performing LPF processing on the pressure value signal.

The blood pressure calculation unit 102 receives the volume pulse wave signal that was extracted by the HPF unit, and performs processing on the received volume pulse wave signal in accordance with a predetermined procedure so as to calculate a maximum blood pressure (SBP (Systolic Blood Pressure)) and a minimum blood pressure (DBP (Diastolic Blood Pressure)), and also calculates the pulse rate in accordance with a known procedure. The blood pressure calculation procedure is envisioned to conform to an oscillometric method, in which pressure is applied to the measurement site by the cuff 20 up to a predetermined pressure, and the blood pressure is measured based on the cuff pressure that is detected as the pressure is then gradually reduced, but there is no limitation to the calculation method.

The oxygen saturation level measurement control unit 200 includes a clock 201 that outputs a clock signal that is synchronized with the time output by the timer 43, a pulse wave amplitude calculation unit 202, a pulse wave amplitude comparison unit 203, and the oxygen saturation level calculation unit 204.

The oxygen saturation level measurement control unit 200 controls the light emitting element drive circuit 52 at a timing defined by the clock 201 such that the light emitting elements 501 and 502 alternatingly emit two wavelengths of infrared light. Infrared light that passes through the subject measurement site and arrives at the light receiving element 503 is detected by the light receiving element 503. At that time, variation in arterial volume that accompanies pulsation of the intra-arterial pressure is reflected as change in the amount of transmitted light in the output from the light receiving element 503. This is called a photoelectric pulse wave (referred to hereinafter as simply "pulse wave"). When pulse wave signals are sent from the light receiving element 503 to the amplification and A/D conversion circuit 53, the pulse waves for different wavelengths are separately amplified and subjected to A/D conversion at a timing defined by the clock 201. The A/D converted pulse wave signals are then sent to the pulse wave amplitude calculation unit 202.

The pulse wave amplitude calculation unit 202 detects, in units of beats, the pulse waves obtained by the amplification and A/D conversion circuit 53, and calculates the amplitudes of the respective pulse waves. The pulse wave amplitude comparison unit 203 obtains the ratio of the amplitudes of the two wavelengths of pulse waves that were calculated by the pulse wave amplitude calculation unit 202. The oxygen saturation level calculation unit 204 calculates the oxygen saturation level in the blood based on the pulse wave amplitude ratio that was calculated. The oxygen saturation level calculation unit 204 then calculates the blood oxygen saturation level of the subject based on a relationship between pulse wave amplitude ratios and oxygen saturation levels that is stored in the memory unit 39 in advance. The blood oxygen saturation level is calculated every five seconds, for example, and the calculated blood oxygen saturation level data is recorded along with pointers i in an internal memory of the CPU 1000.

In the present embodiment, the light emitting elements 501 and 502, the light receiving element 503, the light emitting element drive circuit 52, the amplification and A/D conversion circuit 53, and the oxygen saturation level measurement control unit 200 function as an oxygen saturation level measurement unit for measuring the blood oxygen saturation level. Note that the configuration of the oxygen saturation level measurement unit and the method of calculating the blood oxygen saturation level that are employed in the cardiovascular risk evaluation apparatus 1 according to the present invention are not intended to be limited to those described above.

As shown in FIG. 3, the hypoxic acquisition unit 300 includes a threshold value determination unit 301, a judgment unit 302 in which a comparison unit 305 is included, a low oxygen amount calculation unit 303, a trigger output unit 304 for outputting a trigger signal TR (abbreviated as "trigger TR" hereinafter) based on output from the judgment unit 302, and an interval judgment unit 306 for outputting a measurement start instruction signal IT while monitoring the trigger TR. The trigger output unit 304 causes the blood pressure measurement unit 100 to start blood pressure measurement by outputting the trigger TR based on a comparison result from the comparison unit 305.

As shown in FIG. 4, the indicator detection unit 700 includes a differential blood pressure calculation unit 701, a low oxygen sensitivity calculation unit 702, and a nocturnal hypertension judgment unit 703.

Memory Configuration

As shown in FIG. 5, the memory unit 39 has a measured data storage portion 391 and an indicator storage portion 392 for each subject.

As shown in FIG. 6, the measured data storage portions 391 store measured data in a database format. Specifically, ID data for uniquely identifying the corresponding subject, and one or more records R are stored. Each record R includes No. data for uniquely identifying the record, time data indicating the measurement time, as well as a blood oxygen saturation level (a later-described low oxygen amount Sp or mean MSp), a systolic blood pressure SBP, a diastolic blood pressure DBP, and a pulse rate PL that were measured (or calculated) at that measurement time, along with a flag F. The flag F is for identifying whether the blood oxygen saturation level for that record R is the low oxygen amount Sp or the mean MSp.

As shown in FIG. 7, the indicator storage portions 392 store cardiovascular evaluation indicator data in a database format. Specifically, ID data for uniquely identifying the corresponding subject, and one or more records R are stored. Each record R includes No. data for uniquely identifying the record, time data indicating the measurement time, as well as differential blood pressure DF calculated by the differential blood pressure calculation unit 701 at that time, a low oxygen sensitivity OS calculated by the low oxygen sensitivity calculation unit 702, and a judgment value NH that indicates the result of the judgment made by the nocturnal hypertension judgment unit 703. The judgment value NH is set to "1" if it is judged that the subject suffers from nocturnal hypertension based on the systolic blood pressure SBP measured at that time, and otherwise is set to "0".

Although these types of data are stored in association with each other using the records R in FIGS. 6 and 7, they are not limited to a storage format that uses the records R, as long as they can be associated with each other.

The following describes measurement processing with reference to the flowchart in FIG. 8A. A program that conforms to this flowchart is stored in advance in a predetermined storage area of the memory unit 39, and functionality that conforms to this processing flowchart is realized by the CPU 1000 reading out that program from the memory unit 39 and executing it. The graph in FIG. 8B shows change in the blood oxygen saturation level of a subject as time elapses in the measurement processing shown in FIG. 8A. In this graph, elapsed time is plotted on the horizontal axis, and the blood oxygen saturation level (%) is plotted on the vertical axis.

When measurement is to be performed, it is envisioned that the cuff 20 and the sensor unit 50 will be fitted on the subject as shown in FIG. 9. In order to evaluate the OSA cardiovascular risk of the subject, the subject operates the switch 41C for starting measurement before sleeping, and operates the switch 41D for ending measurement upon getting up.

First, when the subject operates the switch 41C, the operation reception unit 900 receives that operation and outputs a measurement start instruction in accordance with the operation. At this time, the subject operates the switch 41B and inputs their ID data.

When the measurement instruction is input, the oxygen saturation level measurement control unit 200 starts blood oxygen saturation level calculation. The blood oxygen saturation level is calculated every 5 sec, for example, and is recorded in an internal memory of the CPU 1000 as a blood oxygen saturation level SpO2(i). Here, in a predetermined period immediately after the start of sleep (period shorter than a period T1 in FIG. 8B), the subject generally breathes normally (i.e., is not in an OSA state), and therefore the blood oxygen saturation level SpO2(i) indicates a sufficient oxygen amount.

The threshold value determination unit 301 of the hypoxic acquisition unit 300 determines a threshold value TH for judging whether or not the blood oxygen saturation level indicates a low oxygen amount, that is to say, whether or not an apnea attack is occurring (step S1). Specifically, the mean value is calculated for the blood oxygen saturation levels SpO2(i) stored in the internal memory in the aforementioned predetermined period (e.g., 1 minute) since when the measurement instruction was input, and the value obtained by subtracting 10 from the mean value is determined to be the threshold value TH (step S1). This determination method is merely one example, and the present invention is not limited to this. In this way, the threshold value TH for making an apnea attack judgment may be determined individually for each subject, or a threshold value TH to be applied to all subjects in common may be determined in advance.

When the threshold value TH is determined by the threshold value determination unit 301, the determined threshold value TH is given to the judgment unit 302. The judgment unit 302 judges whether or not the blood oxygen saturation level SpO2(i) indicates a value that is lower than the threshold value TH (step S3).

Specifically, the comparison unit 305 reads out the blood oxygen saturation level SpO2(i) from the internal memory in the measurement order (i.e., in accordance with the value of the point i), and compares the readout blood oxygen saturation level SpO2(i) with the threshold value TH. Based on the comparison result, the judgment unit 302 judges whether the blood oxygen saturation level SpO2(i) is lower than the threshold value TH, or higher than or equal thereto. If it is judged that the blood oxygen saturation level SpO2(i) is lower than the threshold value TH (YES in step S3), the comparison unit 302 gives a trigger TR output instruction to the trigger output unit 304, and gives a calculation instruction to the low oxygen amount calculation unit 303.

In response to the instruction, the trigger output unit 304 outputs the trigger TR to the blood pressure measurement unit 100. In response to the trigger TR, the blood pressure measurement unit 100 starts blood pressure measurement in accordance with an apnea attack. When blood pressure measurement starts, the internal pressure of the cuff 20 is raised to a predetermined pressure and then gradually reduced. Blood pressure measurement data (systolic blood pressure SBP, diastolic blood pressure DBP, and pulse rate PL) is calculated based on the cuff pressure that is detected in the depressurization process. Note that blood pressure measurement may be performed in the pressurization process. The calculated blood pressure measurement data is output to the storage processing unit 500 (step S15). Also, in response to the calculation instruction that was received, the low oxygen amount calculation unit 303 calculates a low oxygen amount Sp(i) in an apnea attack, and outputs the calculated low oxygen amount Sp(i) to the storage processing unit 500 (step S17).

Here, the low oxygen amount Sp(i) indicates the lowest value for the blood oxygen saturation level SpO2(i) in the internal memory during one apnea attack. Based on the blood oxygen saturation levels SpO2(i) stored in a time-series in the internal memory, the low oxygen amount calculation unit 303 determines the lowest value using the blood oxygen saturation level SpO2(i) that was stored at the time when the calculation instruction was input and the blood oxygen saturation level SpO2(i−1) that was previously measured (stored). For example, the lowest value for the blood oxygen saturation level SpO2(i) at the star mark in the graph in FIG. 8B, that is to say the low oxygen amount Sp(i), is detected. When an apnea attack occurs, the low oxygen amount Sp(i) that is the lowest value is thereafter acquired multiple times while the apnea attack is occurring, as shown by the arrows in the graph. The blood pressure measurement data that is measured when each low oxygen amount Sp(i) is measured is acquired.

The storage processing unit 500 stores the received blood pressure measurement data, the low oxygen amount Sp(i), and the current time data T output by the timer 43 in association with each other as a record R in the measured data storage portion 391 that corresponds to the ID data of the corresponding subject (step S19). The flag F of the record R stored at this time is set to "0", which indicates that the measured data was acquired in a hypoxic period.

Thereafter, based on an instruction signal from the operation reception unit 900, the CPU 1000 judges whether the subject operated the switch 41D of the operation unit 41 for ending measurement (step S21). If it is judged that the switch 41D was operated (YES in step S21), in accordance with an instruction signal from the operation reception unit 900, the indicator detection unit 700 calculates a cardiovascular risk evaluation indicator such as low oxygen sensitivity, and outputs the indicator to the storage processing unit 500. The storage processing unit 500 stores the input indicator and time data from the timer 43 in association with each other as a record R in the indicator storage portion 392 that corresponds to the ID of the corresponding subject (step S23). The display information generation unit 800 reads out a record R from the storage unit 500, generates image information representing the indicator in the record R, and outputs the image information to the display control unit 850. The display control unit 850 displays the image information on the display unit 40 (step S25). Processing then ends. Although the acquired indicator is output to the display unit 40 here, it may be output to an output unit such as a printer or an audio unit.

If it is judged that the switch 41D has not been operated (NO in step S21), the procedure returns to step S3, and processing is similarly repeated from that step. Note that details of the indicator calculation procedure will be described later.

On the other hand, if it is judged in step S3 that the blood oxygen saturation level SpO2(i) is higher than or equal to the threshold value TH (NO in step S3), processing for interval blood pressure measurement is started. In other words, the interval judgment unit 306 judges whether the subject is in a non-hypoxic period, which is not a hypoxic period in an apnea attack (step S5).

Specifically, the interval judgment unit 306 monitors the trigger TR and judges, based on output from the timer 43, whether a period of no output of the trigger TR has continued for a certain period of time (e.g., 30 minutes) since when measurement started or since the output of the instruction signal IT for starting the previous measurement. If it is judged that the period of no trigger TR output continued for the certain period of time (YES in step S5), the IT is output to the blood pressure measurement unit 100 and the non-hypoxic acquisition unit 400.

Here, the interval blood pressure measurement is performed every 30 minutes since pressurization and depressurization of the cuff 20 at the measurement site during blood pressure measurement has the possibility of disturbing the subject's sleep, but there is no limitation to 30 minutes. Also, a configuration is possible in which the interval can be set variably.

In response to the input of the instruction signal IT, the blood pressure measurement unit 100 starts blood pressure measurement, outputs the acquired blood pressure measurement data to the storage processing unit 500 (step S7), and in response to the input of the instruction signal IT, the mean calculation unit 401 of the non-hypoxic acquisition unit 400 reads out most recently stored blood oxygen saturation levels SpO2(i) (e.g., stored in the past minute) from the internal memory, calculates a mean MSp(i) based on the readout blood oxygen saturation levels SpO2(i), and outputs the calculated mean MSp(i) to the storage processing unit 500 (step S9).

The storage processing unit 500 stores the received blood pressure measurement data, the mean MSp(i), and the current time data T output by the timer 43 in association with each other as a record R in the measured data storage portion 391 that corresponds to the ID of the corresponding subject in the memory unit 39 (step S19). The mean MSp(i) is considered to be the blood oxygen saturation level SpO2(i) that was measured when that blood pressure measurement data was measured. Although a mean value is used here, it is sufficient to use any representative value, such as a median value or mode value. The flag F of the record R stored at this time is set to "1", which indicates that the measured data (mean MSp(i)) was acquired in a non-hypoxic period. Thereafter, the procedure returns to step S21.

On the other hand, if it is judged that the period has not continued for the certain period of time (NO in step S5), the procedure moves to step S21 without starting blood pressure measurement or the calculation of the mean MSp(i) for blood oxygen saturation levels SpO2(i).

Here, the CPU 1000 has a function for judging whether or not the subject is sleeping based on the operation of a switch of the operation unit 41, which is received by the operation reception unit 900, but the judgment method is not limited to this. For example, the judgment may be made using a timer. Alternatively, a configuration is possible in which the cuff 20 or the sensor unit 50 is provided with a sensor for detecting attachment to and detachment from the measurement site, and the judgment is made based on output from that sensor. As another alternative, a configuration is possible in which the body temperature of the subject is measured, and the judgment is made based on a change in body temperature, with focus placed on the fact that the subject's body temperature decreases during sleep.

In the processing according to this flowchart, the hypoxic acquisition unit 300 acquires one or more measurement results that include the low oxygen amount Sp(i), which is the blood oxygen saturation level that was measured in a hypoxic period in which the blood oxygen saturation level SpO2(i) of the subject is lower than the threshold value TH, and also the blood pressure that was measured when that blood oxygen saturation level was measured. Also, the non-hypoxic acquisition unit 400 acquires one or more measurement results that include the blood pressure that was measured in a non-hypoxic period in which the blood oxygen saturation level SpO2 (i) of the subject is higher than or equal to the threshold value TH, and also the blood oxygen saturation level (mean MSp(i)) that was measured when that blood pressure was measured. The indicator detection unit 700 then calculates the indicator using the measurement results acquired in this way.

Indicator Calculation

In step S23, the indicator detection unit 700 reads out records R from the measured data storage portion 391 of the subject in the memory unit 39, and calculates indicators based on the data in the readout records R. Specifically, cardiovascular risk evaluation indicators for the subject are acquired based on the relationship between blood oxygen saturation level and blood pressure, which is based on the data in one or more measurement result records R acquired by the hypoxic acquisition unit 300 and the data in one or more measurement result records R acquired by the non-hypoxic acquisition unit 400.

Based on the above-described relationship, the differential blood pressure calculation unit 701 calculates the difference between the blood pressure measured in the non-hypoxic state and the blood pressure measured in the hypoxic state, as a cardiovascular risk evaluation indicator. Based on the above-described relationship, the low oxygen sensitivity calculation unit 702 acquires the low oxygen sensitivity of the subject as a cardiovascular risk evaluation indicator. The low oxygen sensitivity referred to here represents the extent of the rise in blood pressure in response to a certain amount of decrease in oxygen saturation level. Based on the above-described relationship, the nocturnal hypertension judgment unit 703 judges whether or not the blood pressure of the subject corresponds to nocturnal hypertension.

Although three types of examples have been given for cardiovascular risk evaluation indicators that are related to the blood pressure load deriving from the low blood oxygen saturation level, the indicators are not limited to these examples.

Low Oxygen Sensitivity

Figure 10A:
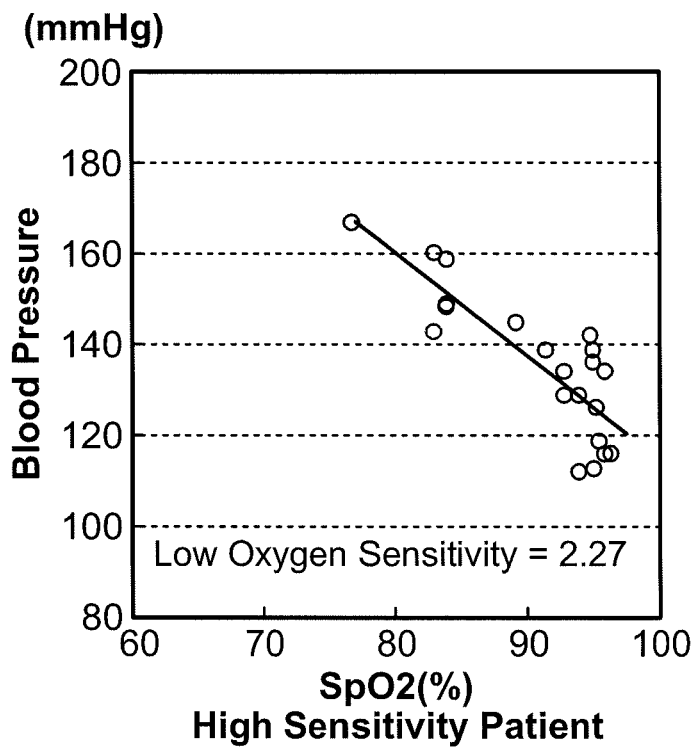
FIGS. 10A and 10B are diagrams showing oxygen sensitivity.
Figure 10B:
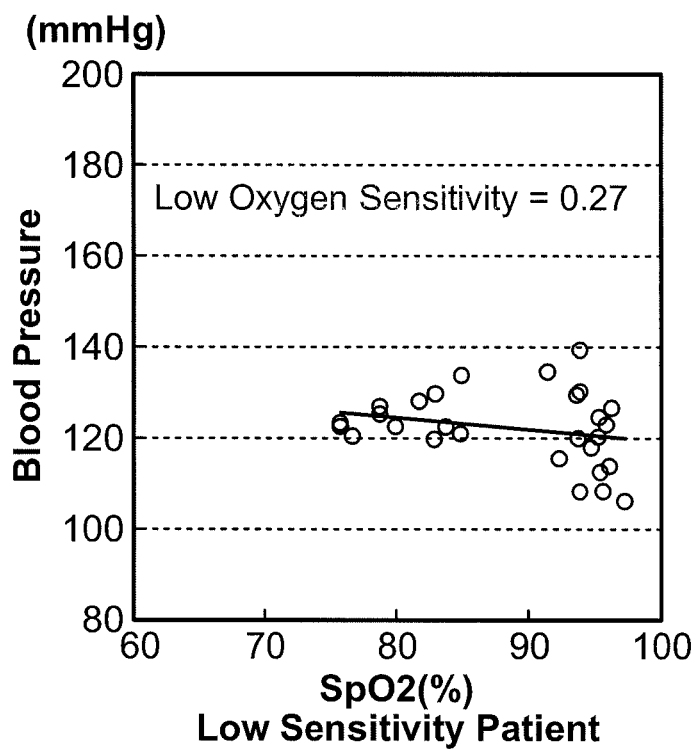

Based on the data in the records R that were read out from the measured data storage portion 391, that is to say, based on the systolic blood pressures SBP associated with the blood oxygen saturation levels (low oxygen amounts Sp(i) and means MSp(i)), the low oxygen sensitivity calculation unit 702 calculates a regression line expression (called a relational expression) that indicates the relationship between the two, as shown in the graphs in FIGS. 10A and 10B (the blood pressure plotted on the vertical axis, and the blood oxygen saturation level SpO2 plotted on the horizontal axis), for example. As shown in FIGS. 10A and 10B, the relational expression that is obtained indicates the difference between the measurement results acquired by the hypoxic acquisition unit 300 and the measurement results acquired by the non-hypoxic acquisition unit 400. The low oxygen sensitivity calculation unit 702 calculates the slope of the line indicated by the relational expression as the low oxygen sensitivity. The data in FIGS. 10A and 10B indicates data acquired from two subjects by experimentation performed by the inventors in accordance with the flowchart in FIG. 8A. Note that methods that are normally widely used in statistics can be applied as the method for calculating the regression line relational expression. FIG. 10A illustrates the case where the low oxygen sensitivity is high, and FIG. 10B illustrates the case where it is low.

This calculation method is merely one example, and the low oxygen sensitivity may be obtained from the slope of a linear expression (relational expression) that connects two points, namely the mean value of the trigger blood pressures (systolic blood pressures SBP associated with the low oxygen amounts Sp(i)) and the mean value of the interval blood pressures (systolic blood pressures SBP associated with the means MSp(i)). Alternatively, it may be obtained from the slope of the relational expression of a line that connects two points, namely the highest three-point trigger blood pressure mean value and the lowest three-point interval blood pressure mean value, or may be obtained using another method.

The indicators calculated in this way (low oxygen sensitivity value and scatter diagram shown in FIGS. 10A and 10B) are displayed on the display unit via the display information generation unit 800 and the display control unit 850. At this time, the low oxygen sensitivity may be displayed as an absolute value, may be displayed in the format of a comparison with a normal value, or may be displayed as a level representing the extent of the condition (the extent of risk to the cardiovascular system (possibility of stroke)).

Focusing on the fact that the subject in FIG. 10A had a higher low oxygen sensitivity value than the subject in FIG. 10B, and the rise in blood pressure in response to a decrease in blood oxygen saturation level was more noticeable, the inventors found that the higher the low oxygen sensitivity value is, the higher the pressure load on the cardiovascular system during an apnea attack is, and the higher the risk to the cardiovascular system is predicted to be.

Figure 11:
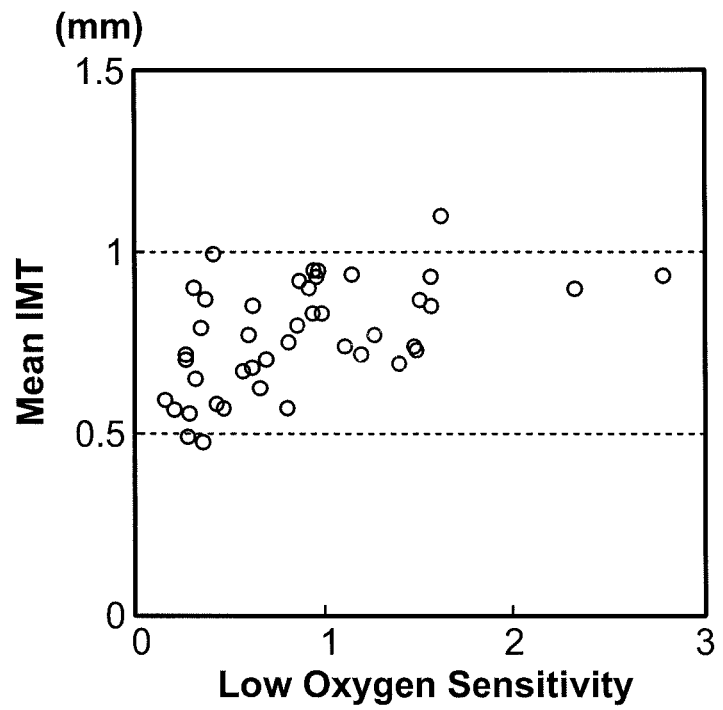
FIG. 11 is a diagram showing the correlation between low oxygen sensitivity and mean carotid artery thickness (mean IMT).

In order to substantiate this, the inventors verified the correlation between the low oxygen sensitivity and the mean value of the carotid artery thickness (mean IMT) indicating the extent of arterial sclerosis, by plotting measurement data from 46 subjects in the graph in FIG. 11. In the graph in FIG. 11, the mean value of the carotid artery thickness is plotted on the vertical axis (y axis), and the low oxygen sensitivity is plotted on the horizontal axis (x axis). As shown in FIG. 11, based on the fact that the two values have a significant correlation, it was shown that low oxygen sensitivity is a favorable indicator for evaluating (estimating) cardiovascular risk in a sleep apnea sufferer.

Differential Blood Pressure and Nocturnal Hypertension

Figure 12:
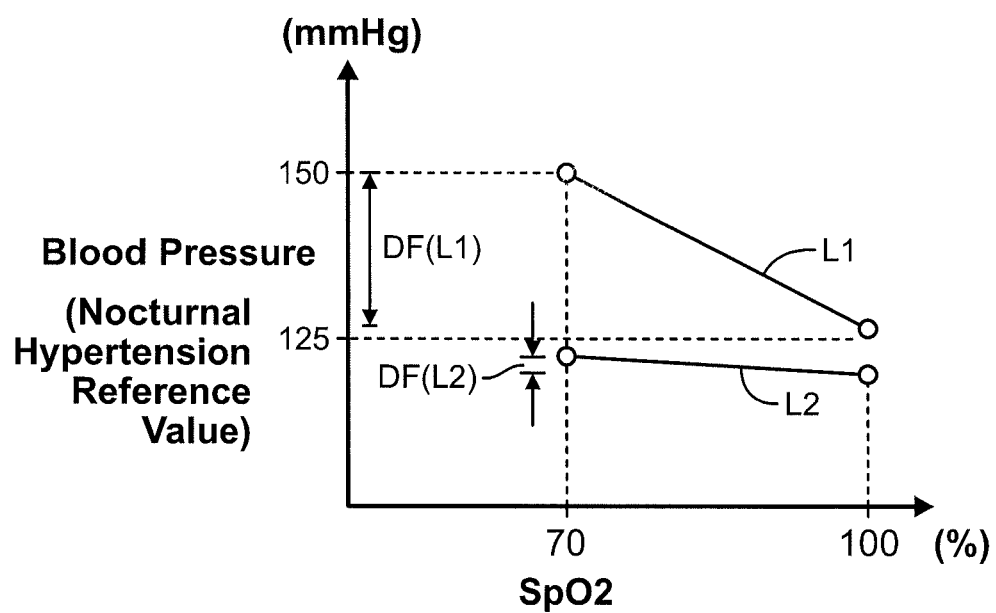
FIG. 12 is a diagram for describing differential blood pressure and nocturnal hypertension.

Similarly to the above description, based on the data in the records R that were read out from the measured data storage portion 391, that is to say, based on the systolic blood pressures SBP associated with the blood oxygen saturation levels (low oxygen amounts Sp(i) and means MSp(i)), the differential blood pressure calculation unit 701 calculates a linear relational expression as shown in the graph in FIG. 12 (the blood pressure plotted on the vertical axis, and the blood oxygen saturation level SpO2 plotted on the horizontal axis). FIG. 12 shows lines L1 and L2 measured for two subjects by performing experimentation in accordance with the flowchart in FIG. 8A. Similarly to the lines shown in FIGS. 10A and 10B, these lines connect two points, namely the mean value of the trigger blood pressures (systolic blood pressures SBP associated with the low oxygen amounts Sp(i)) and the mean value of the interval blood pressures (systolic blood pressures SBP associated with the means MSp(i)).

Based on the linear relational expressions, the differential blood pressure calculation unit 701 calculates the difference between the trigger blood pressure and the interval blood pressure as a differential blood pressure DF. It can be seen in FIG. 12 that since the line L1 having a high slope (low oxygen sensitivity) indicated by the relational expression has a high differential blood pressure DF(L1), and the line L2 having a low slope (low oxygen sensitivity) has a low differential blood pressure DF(L2), low oxygen sensitivity and differential blood pressure are correlated with each other.

The nocturnal hypertension judgment unit 703 compares the mean value of the trigger blood pressures (systolic blood pressures SBP associated with the low oxygen amounts Sp(i)) with a nocturnal hypertension reference value (125 mmHg). Upon judging that the mean value is greater than or equal to 125 mmHg based on the comparison result, the nocturnal hypertension judgment unit 703 estimates that the subject suffers from nocturnal hypertension and outputs the judgment value NH (="1"), and upon judging that the mean value is less than 125 mmHg, the nocturnal hypertension judgment unit 703 estimates that the subject does not suffer from nocturnal hypertension and outputs the judgment value NH (="0").

Example of Display

Figure 13:
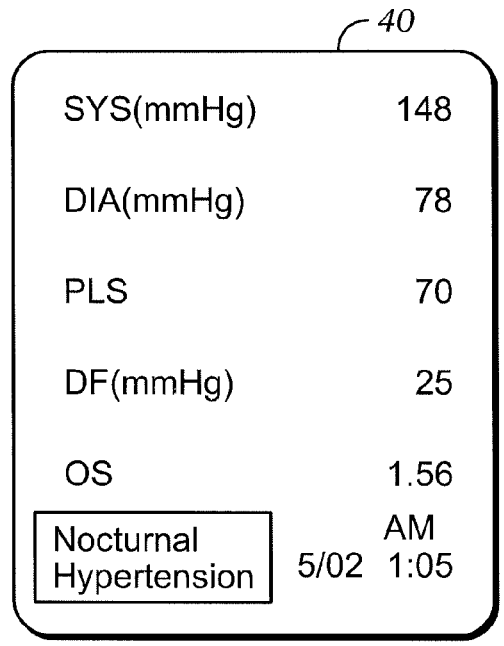
FIG. 13 is a diagram showing an example of a display according to the embodiment.

FIG. 13 shows an example of the display of measurement results on the display unit 40. As shown in FIG. 13, values for the systolic blood pressure, the diastolic blood pressure, the pulse rate, the differential blood pressure, and the low oxygen sensitivity are displayed on the display unit 40 as measurement results, and a mark indicating whether or not the subject suffers from nocturnal hypertension is also displayed. Although the systolic blood pressure, the diastolic blood pressure, and the pulse rate are indicated by mean values in the measurement period, they may be the systolic blood pressure, the diastolic blood pressure, and the pulse rate when the highest systolic blood pressure value was measured. The measurement time for these measurement data pieces is also displayed on the display unit 40. In addition to the indicators, advice regarding a drug prescription may also be displayed based on the indicators.

Information Processing Apparatus

Figure 14:
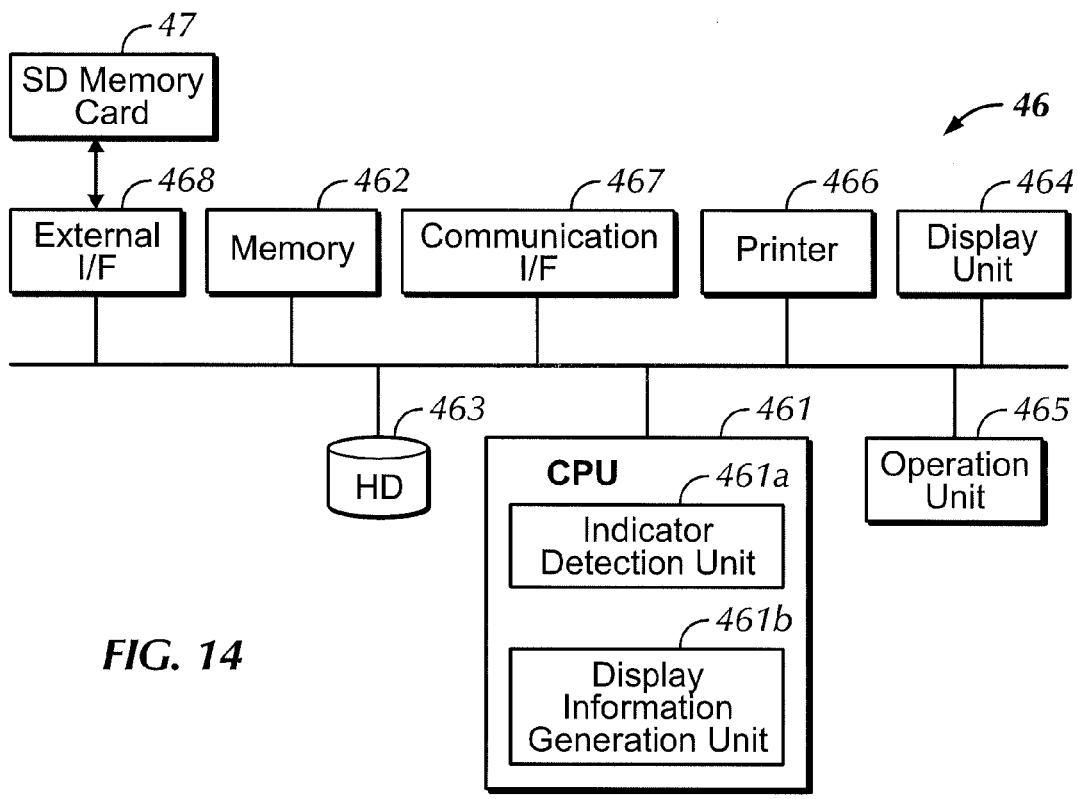
FIG. 14 shows a configuration of an information processing apparatus according to the embodiment.

FIG. 14 shows an example of the information processing apparatus 46. The information processing apparatus 46 functions as a data processing apparatus for processing measurement data obtained by the cardiovascular risk evaluation apparatus 1.

The information processing apparatus 46 includes a CPU 461, a memory 462 for storing programs and data, a hard disk 463, a display unit 464, an operation unit 465 for receiving user operations, a printer 466, a communication I/F (interface) 467 for communication with external devices (including the cardiovascular risk evaluation apparatus 1), and an external I/F 468 to and from which various types of recording media such as a SD memory card 47 can be mounted and removed, and that accesses the mounted recording medium under control of the CPU 461.

Data measured by the cardiovascular risk evaluation apparatus 1 is received by the communication I/F 467. Alternatively, the SD memory card 47 with measurement data recorded thereon is mounted to the external I/F 468, and measurement data is acquired by being read out from the SD memory card 47. The measurement data received or acquired in this way is stored in the memory 462 or the like.

The CPU 461 includes an indicator detection unit 461A that calculates the above-described indicators based on the measurement data stored in the memory 462, and a display information generation unit 461B that generates display information for displaying the calculated indicators. The generated display information is displayed on the display unit 464. Note that the display information may be transmitted to the cardiovascular risk evaluation apparatus 1 and displayed on the display unit 40 of the cardiovascular risk evaluation apparatus 1.

In this way, an apparatus that is external to the cardiovascular risk evaluation apparatus 1, such as the medical information processing apparatus 46, can acquire measurement data and calculate and display indicators.

The method corresponding to the flowchart in FIG. 8A performed by the cardiovascular risk evaluation apparatus 1 of the present invention can be provided as a program. Such a program can be provided in the form of a program product that is recorded on a computer-readable recording medium such as a flexible disk, a CD-ROM, a ROM, a RAM, or a memory card that is supplied to a computer. Alternatively, the program can be provided in the form of being recorded on a recording medium such as a hard disk built into a computer. The program can also be provided by downloading via a network. For example, in the configuration shown in FIG. 1, the cardiovascular risk evaluation apparatus 1 that includes the CPU 1000 and has the functionality of a computer can be supplied with the program using any of various types of recording media, such as the SD memory card 47. The CPU 1000 reads out the program stored on the recording medium via the external I/F 45 and executes it. Also, in the configuration shown in FIG. 14, the information processing apparatus 46 can be supplied with the program using any of various types of recording media, such as the SD memory card 47. The CPU 461 reads out the program stored on the recording medium via the external I/F 48 and executes it.

The program product that is provided is installed in a program storage unit such as a hard disk, and is read out and executed by a CPU. Note that the program product includes the program itself and the recording medium on which the program is recorded.

Variation

Although the processing in FIG. 8A is envisioned to be performed while the subject is sleeping, it is not limited to being performed while the subject is sleeping. For example, a configuration is possible in which measurement data is acquired by cyclically repeating a period of respiration and a period of stopped respiration while the subject is awake.

Also, although trigger blood pressure measurement continues when interval blood pressure measurement is performed, and interval blood pressure measurement is performed in a period in which trigger blood pressure measurement is not performed in FIG. 8A, it is possible to separately acquire measurement data for the non-hypoxic state through interval blood pressure measurement. In other words, measurement data for the non-hypoxic state may be acquired when the subject is in a waking resting state.

Also, a configuration is possible in which the threshold value TH is set to a low value for a subject whose low oxygen sensitivity is high, and set to a high value for a subject whose low oxygen sensitivity is high.

Figure 15:
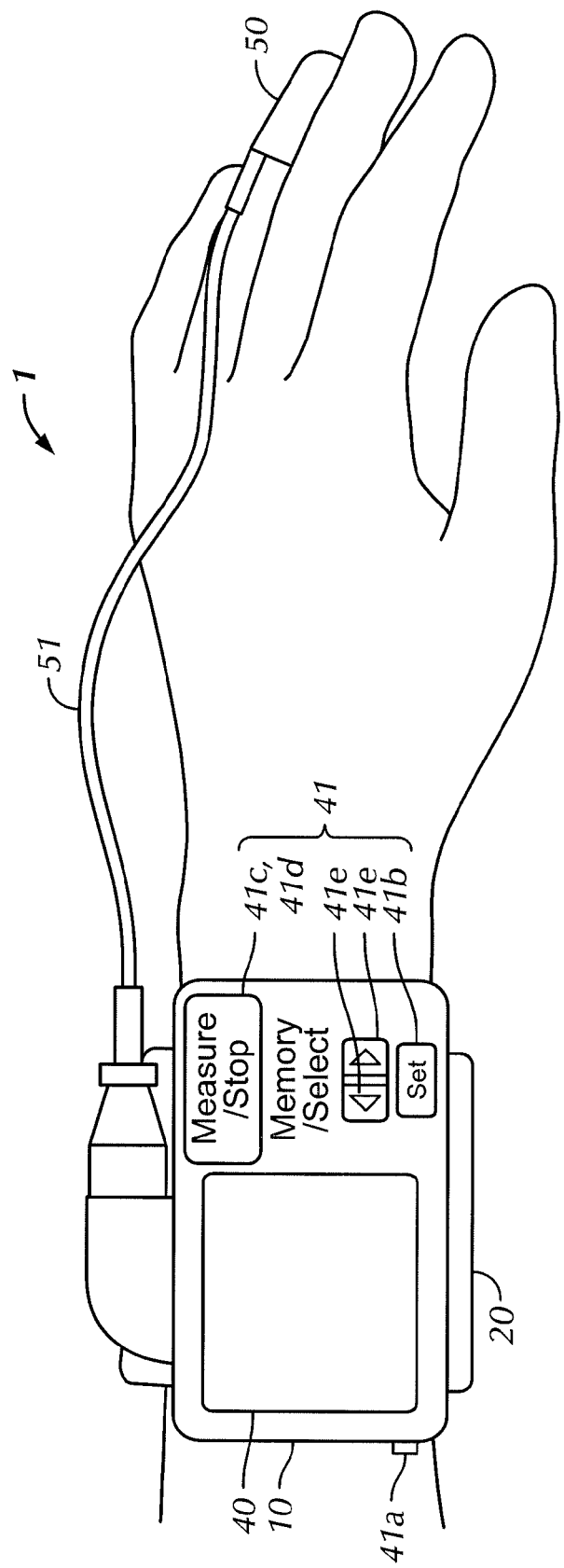
FIG. 15 is a diagram showing a wrist-mounted cardiovascular risk evaluation apparatus according to a variation of the embodiment.

Although the cardiovascular risk evaluation apparatus 1 is of the type in which it is stationarily provided on a desk in the present embodiment, it may be a wrist-mounted type as shown in FIG. 15. In FIG. 15, the blood pressure measurement site is the wrist portion, the cuff 20 is wrapped around the wrist, and the body unit 10 and cuff 20 are configured so as to be integrated. Various types of switches corresponding to the operation unit 41 are provided on the surface of the casing of the body unit 10.

The embodiments disclosed here are to be considered as an example in all respects and not as limiting in any way. The scope of the present invention is defined by the claims, not the above description, and all changes that come within the meaning and range of equivalency of the claims are intended to be embraced therein. Also, all possible combinations of the embodiments described above are intended to be embraced in the present invention.

REFERENCE SIGNS LIST

1 Cardiovascular risk evaluation apparatus
46 Information processing apparatus
50 Sensor unit
100 Blood pressure measurement unit
200 Oxygen saturation level measurement control unit
204 Oxygen saturation level calculation unit
300 Hypoxic acquisition unit
301 Threshold value determination unit
302 Judgment unit
303 Low oxygen amount calculation unit
304 Trigger output unit
305 Comparison unit
306 Interval judgment unit
391 Measured data storage portion
392 Indicator storage portion
400 Non-hypoxic acquisition unit
401 Mean calculation unit
461A, 700 Indicator detection unit
461B, 800 Display information generation unit
701 Differential blood pressure calculation unit
702 Low oxygen sensitivity calculation unit
703 Nocturnal hypertension judgment unit

The invention claimed is:

1. A cardiovascular risk evaluation apparatus comprising:
a body unit comprising: an air system; a light emitting element drive circuit; a processor; and a memory;
a cuff connected to the air system of the body unit by an air tube;
a hypoxic acquisition unit within the processor of the body unit that acquires a measurement result that includes a blood oxygen saturation level and a blood pressure, which are measured in a hypoxic period in which the blood oxygen saturation level of a subject is lower than a threshold value;
a non-hypoxic acquisition unit within the processor of the body unit that acquires a measurement result that includes a blood oxygen saturation level and a blood pressure, which are measured in a non-hypoxic period of the blood oxygen saturation level of the subject;
an indicator detection unit within the processor of the body unit that calculates a cardiovascular risk evaluation indicator for the subject based on a relationship between blood oxygen saturation level and blood pressure that is based on the measurement result acquired by the hypoxic acquisition unit and the measurement result acquired by the non-hypoxic acquisition unit,
wherein the indicator detection unit calculates the cardiovascular risk evaluation indicator for the subject based on a relational expression that indicates a difference between the measurement result acquired by the hypoxic acquisition unit and the measurement result acquired by the non-hypoxic acquisition unit; and
a display information generation unit within the processor of the body unit that outputs the cardiovascular risk evaluation indicator to an output unit that is connected to the processor of the body unit,
wherein the processor judges whether or not the subject is sleeping, and wherein the hypoxic acquisition unit acquires a measurement result that includes a blood oxygen saturation level that is measured in a hypoxic period in a case of a judgment that the subject is sleeping, and a blood pressure that was measured when the blood oxygen saturation level was measured.

2. The cardiovascular risk evaluation apparatus according to claim 1, wherein the indicator detection unit calculates a difference between the blood pressure measured in a non-hypoxic state and the blood pressure measured in a hypoxic state based on the relational expression.

3. The cardiovascular risk evaluation apparatus according to claim 1, wherein the non-hypoxic acquisition unit acquires a measurement result that includes a blood oxygen saturation level that is measured in a non-hypoxic period in a case of a judgment that the subject is sleeping, and a blood pressure that was measured when the blood oxygen saturation level was measured.

4. The cardiovascular risk evaluation apparatus according to claim 1, further comprising:
an oxygen saturation level measurement control unit within the processor of the body unit that measures the blood oxygen saturation level of the subject; and
a blood pressure measurement unit within the processor of the body unit that measures the blood pressure of the subject,
wherein the hypoxic acquisition unit compares the blood oxygen saturation level measured by the oxygen saturation level measurement control unit and the threshold value, and causes the blood pressure measurement unit to start blood pressure measurement based on a result of the comparison.

5. The cardiovascular risk evaluation apparatus according to claim 4,
wherein the oxygen saturation level control unit measures the blood oxygen saturation level at a predetermined interval, and
in a case of detection, based on the blood oxygen saturation levels measured at the predetermined interval, that the blood oxygen saturation level is lower than the threshold value, the hypoxic acquisition unit causes the blood pressure measurement unit to start blood pressure measurement.

6. The cardiovascular risk evaluation apparatus according to claim 1, wherein based on the relational expression, the indicator detection unit calculates a low oxygen sensitivity of the subject as the cardiovascular risk evaluation indicator.

7. The cardiovascular risk evaluation apparatus according to claim 1, wherein the hypoxic acquisition unit calculates the threshold value based on the blood oxygen saturation level of the subject that is measured in the non-hypoxic period.

8. A non-transitory computer readable medium storing thereon a program for outputting a cardiovascular risk evaluation indicator, the program causing a processor to execute the steps of:
acquiring a measurement result that includes a blood oxygen saturation level and a blood pressure, which are measured in a hypoxic period in which the blood oxygen saturation level of a subject is lower than a threshold value;
acquiring a measurement result that includes a blood oxygen saturation level and a blood pressure, which are measured in a non-hypoxic period of the blood oxygen saturation level of the subject;
calculating a cardiovascular risk evaluation indicator for the subject based on a relationship between blood oxygen saturation level and blood pressure that is based on the measurement result acquired in the hypoxic period and the measurement result acquired in the non-hypoxic period,
wherein the calculating step further comprises calculating the cardiovascular risk evaluation indicator for the subject based on a relational expression that indicates a difference between the measurement result acquired by the hypoxic acquisition unit and the measurement result acquired by the non-hypoxic acquisition unit;
judging whether or not the subject is sleeping,
wherein the hypoxic acquisition unit acquires a measurement result that includes a blood oxygen saturation level that is measured in a hypoxic period in a case of a judgment that the subject is sleeping, and a blood pressure that was measured when the blood oxygen saturation level was measured; and
outputting the cardiovascular risk evaluation indicator to an output unit that is connected to the processor.

* * * * *